US008758450B2

(12) United States Patent
Hercouet et al.

(10) Patent No.: US 8,758,450 B2
(45) Date of Patent: Jun. 24, 2014

(54) HAIR TREATMENT PROCESS USING A DIRECT EMULSION COMPRISING AN OXIDIZING AGENT AND A DIRECT EMULSION CONTAINING AN ALKALINE AGENT

(75) Inventors: Leila Hercouet, Neuily Plaisance (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/638,940

(22) PCT Filed: Mar. 30, 2011

(86) PCT No.: PCT/EP2011/054885
§ 371 (c)(1),
(2), (4) Date: Oct. 2, 2012

(87) PCT Pub. No.: WO2011/121008
PCT Pub. Date: Oct. 6, 2011

(65) Prior Publication Data
US 2013/0019414 A1    Jan. 24, 2013

Related U.S. Application Data

(60) Provisional application No. 61/324,060, filed on Apr. 14, 2010.

(30) Foreign Application Priority Data

Apr. 2, 2010   (FR) ...................................... 10 52520

(51) Int. Cl.
*A61Q 5/10*   (2006.01)
(52) U.S. Cl.
USPC ................ 8/405; 8/406; 8/501; 8/580; 8/111; 132/202; 132/208
(58) Field of Classification Search
USPC .............. 8/405, 406, 501, 580, 111; 132/202, 132/208
See application file for complete search history.

(56) References Cited

U.S. PATENT DOCUMENTS 5,817,155 A * 10/1998 Yasuda et al. ..................... 8/406
2007/0169285 A1   7/2007 Narasimhan et al.

FOREIGN PATENT DOCUMENTS

JP    2003-81790 A    3/2003

OTHER PUBLICATIONS

Noll, Chapter 1 of Chemistry and Technology of Silicones, Academic Press, 1968, pages Title page, copyright page, contents, and pp. 1-23.
Todd et al., "Silicone Fluids for Cosmetic Formulations," Cosmetics and Toiletries, vol. 91, Jan. 1976, pp. 27-32.
Mitsui et al., "Application of the Phase-Inversion-Temperature Method to the Emulsification of Cosmetics," American Cosmetics and Perfumery, vol. 87, Dec. 1972, pp. 33-36.
Shinoda et al., "The Stability of O/W Type Emulsions as Functions of Temperature and the HLB of Emulsifiers: The Emulsification by PIT-Method," Journal of Colloid and Interface Science, vol. 30, No. 2, Jun. 1969, pp. 258-263.
Forster, et al., "Influence of Microemulsion Phases on the Preparation of Fine-Disperse Emulsions," Advances in Colloid and Interface Science, 58, 1995, pp. 119-149.
International Search Report for Application No. PCT/EP2011/054885, dated Jul. 22, 2011, (2 pages).
Internationl Search Report for Application No. PCT/EP2011/054885, dated Jul. 22, 2011 (2 pages).
English translation of JP Patent Application Publication No. 2003-81790A (Mar. 19, 2003).

* cited by examiner

*Primary Examiner* — Eisa Elhilo
(74) *Attorney, Agent, or Firm* — The Marbury Law Group, PLLC.

(57)    ABSTRACT

The subject of the present invention is therefore a method for the lightening and/or lightening dyeing of keratin materials, which consists in treating the keratin fibers with at least: a) one direct emulsion (A) comprising one or more fatty substances free of carboxylic acid groups, one or more surfactants, an amount of water of greater than 5% by weight of the total weight of the emulsion, and one or more oxidizing agents; and b) one direct emulsion (B) comprising one or more fatty substances free of carboxylic acid groups, one or more surfactants, an amount of water of greater than 5% by weight of the total weight of the emulsion, and one or more alkaline agents; the concentration of fatty substances free of carboxylic acid groups being at least equal to 25% by weight of the total weight of the composition obtained after mixing the two direct emulsions (A) and (B). This process does not have the drawbacks caused by the presence of high contents of alkaline agents, and uses dyeing and/or bleaching compositions having improved lightening properties and that are stable over time, while at the same time remaining at least as effective in terms of the uniformity of the lightening, while at the same time preserving the quality of the keratin fiber.

16 Claims, No Drawings

HAIR TREATMENT PROCESS USING A DIRECT EMULSION COMPRISING AN OXIDIZING AGENT AND A DIRECT EMULSION CONTAINING AN ALKALINE AGENT

This is a national stage application of PCT/EP2011/054885, filed internationally on Mar. 30, 2011, which claims priority to U.S. Provisional Application No. 61/324,060, filed on Apr. 14, 2010, and French Application No. 1052520, filed on Apr. 2, 2010.

The present invention relates to a process for treating keratin materials, especially for lightening and/or dyeing hair, using two particular direct emulsions.

Processes for lightening and/or dyeing keratin materials such as human keratin fibres consist in using an aqueous composition comprising at least one oxidizing agent, under alkaline pH conditions in the vast majority of cases.

Thus, in the oxidation dyeing of hair, oxidizing compositions are mixed with alkaline compositions comprising oxidation dyes (bases and couplers), which are colourless in themselves, to generate coloured compounds and dyes by a process of oxidative condensation. Oxidizing compositions are also used in the direct dyeing of the hair as a mixture with alkaline compositions comprising certain direct dyes that are coloured and colouring, in order to obtain a coloration with a lightening effect on the hair. Among the oxidizing agents conventionally used for dyeing keratin fibres, mention may be made of hydrogen peroxide, persalts such as perborates and persulphates, or compounds capable of producing hydrogen peroxide by hydrolysis, such as urea peroxide, hydrogen peroxide being more particularly preferred.

In hair bleaching, bleaching compositions contain one or more oxidizing agents. The role of these oxidizing agents is to degrade the melanin of the hair, which, depending on the nature of the oxidizing agent present, leads to more or less pronounced lightening of the fibres.

Thus, for relatively weak lightening, the oxidizing agent is generally hydrogen peroxide. When more substantial lightening is desired, peroxygenated salts, for instance persulphates, are usually used, in the presence of hydrogen peroxide.

The bleaching compositions may be aqueous compositions containing alkaline agents (amines or aqueous ammonia) that are mixed at the time of use with an aqueous hydrogen peroxide composition.

These compositions may also be formed from anhydrous products that contain alkaline compounds (amines and alkaline silicates), and a peroxygenated reagent such as ammonium or alkali metal persulphates, perborates or percarbonates, which is diluted at the time of use with an aqueous hydrogen peroxide composition.

One of the difficulties arises from the fact that the lightening and/or dyeing process is performed under alkaline conditions and that the alkaline agent most commonly used is aqueous ammonia. Aqueous ammonia is particularly advantageous in this type of process. Specifically, it makes it possible to adjust the pH of the composition to an alkaline pH to enable activation of the oxidizing agent. It also causes swelling of the keratin fibre, with opening of the scales, which promotes penetration of the oxidant inside the fibre and therefore increases the efficacy of the reaction.

This alkalinizing agent is highly volatile, and this causes unpleasantness to the user on account of the strong and fairly unpleasant odour of ammonia that is given off during the procedure.

Moreover, the amount of ammonia given off requires the use of levels which are greater than those necessary, in order to compensate for this loss. This is not without consequence for the user, who not only remains inconvenienced by the odour but may also be confronted with greater risks of intolerance, such as, for example, irritation of the scalp (stinging sensations).

The option purely and simply of replacing all or some of the aqueous ammonia by one or more other conventional alkalinizing agents does not result in compositions that are as effective as those based on aqueous ammonia, particularly for the reason that these alkalinizing agents do not provide sufficient lightening of the pigmented fibres in the presence of the oxidizing agent.

The introduction of a large amount of oil, in replacement for water, into ready-to-use compositions for dyeing and/or bleaching keratin fibres allows an improvement in the performance of the lightening active agents. However, the introduction of a large amount of oil into the oxidizing composition or into the alkaline composition leads to destabilization of the composition, the phases of which separate after a few days.

The aim of the present invention is to provide lightening and/or dyeing processes that do not have the drawbacks of those carried out with existing compositions, drawbacks caused by the presence of high contents of aqueous ammonia, and that use dyeing and/or bleaching compositions having improved lightening properties and that are stable over time, while at the same time remaining at least as effective in terms of the uniformity of the lightening, while at the same time preserving the quality of the keratin fibre.

These aims and others are achieved by the present invention, one subject of which is thus a process for the lightening and/or lightening dyeing of keratin materials, which consists in treating the keratin materials with at least a) one direct emulsion (A) comprising one or more fatty substances free of carboxylic acid groups, one or more surfactants, an amount of water of greater than 5% by weight of the total weight of the emulsion, and one or more oxidizing agents, and b) one direct emulsion (B) comprising one or more fatty substances free of carboxylic acid groups, one or more surfactants, an amount of water of greater than 5% by weight of the total weight of the emulsion, and one or more alkaline agents; the concentration of fatty substances free of carboxylic acid groups being at least equal to 25% by weight of the total weight of the composition obtained after mixing the two direct emulsions (A) and (B).

The invention also relates to a multi-compartment device comprising, in one of the compartments, the direct emulsion (A), and, in another compartment, the direct emulsion (B).

In the context of the invention, a direct emulsion is an oil-in-water emulsion.

In the text hereinbelow, unless otherwise indicated, the limits of a range of values are included in that range.

The keratin materials treated by the process according to the invention are especially hair. The process of the invention especially makes it possible to obtain a good level of lightening of hair, while at the same time preserving good quality of the keratin fibres.

The emulsions (A) and (B) each comprise water in an amount of greater than 5% by weight, preferably more than 10% by weight and more advantageously still more than 20% by weight of the total weight of the emulsion.

According to one particular embodiment of the invention, the emulsions (A) and (B) each have a water content of less than 50% by weight, preferably between 10 and 50% by weight relative to the total weight of the emulsion.

The oil-in-water emulsions useful in the present invention comprise one or more fatty substances free of carboxylic acid groups.

For the purposes of the present invention, the term "fatty substance" means an organic compound that is insoluble in water at ordinary temperature (25° C.) and at atmospheric pressure (760 mmHg) (solubility of less than 5%, preferably 1% and more preferably still 0.1%). In addition, under the same temperature and pressure conditions, the fatty substances are soluble in organic solvents such as chloroform, ethanol or benzene, for example.

The fatty substances of the invention are not oxyalkylenated.

Preferably, the fatty substances of the invention are chosen from hydrocarbons, fatty alcohols, fatty esters, silicones and fatty ethers, or mixtures thereof.

The fatty substances of the invention may be liquid or non-liquid at room temperature (25° C.) and at atmospheric pressure (760 mmHg; i.e. $1.013 \times 10^5$ Pa).

The liquid fatty substances of the invention preferably have a viscosity of less than or equal to 2 Pa·s, better still less than or equal to 1 Pa·s and even better still less than or equal to 0.1 Pa·s at a temperature of 25° C. and at a shear rate of $1\ s^{-1}$.

The term "liquid hydrocarbon" means a hydrocarbon composed solely of carbon and hydrogen atoms, which is liquid at ordinary temperature (25° C.) and at atmospheric pressure (760 mmHg; i.e. $1.013 \times 10^5$ Pa).

More particularly, the liquid hydrocarbons are chosen from:
- linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane.
- linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as Parleam®, and squalane.

In one preferred variant, the liquid hydrocarbon(s) is (are) chosen from volatile or non-volatile liquid paraffins, and derivatives thereof, and liquid petroleum jelly.

The term "liquid fatty alcohol" means a non-glycerolated and non-oxyalkylenated fatty alcohol that is liquid at ordinary temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention may be saturated or unsaturated.

The saturated liquid fatty alcohols are preferably branched. They may optionally comprise in their structure at least one aromatic or non-aromatic ring. They are preferably acyclic.

More particularly, the liquid saturated fatty alcohols of the invention are chosen from octyldodecanol, isostearyl alcohol and 2-hexyldecanol.

Octyldodecanol is very particularly preferred.

These liquid unsaturated fatty alcohols have at least in their structure at least one double or triple bond. Preferably, the fatty alcohols of the invention bear in their structure one or more double bonds. When several double bonds are present, there are preferably 2 or 3 of them, and they may be conjugated or non-conjugated.

These unsaturated fatty alcohols may be linear or branched.

They may optionally comprise in their structure at least one aromatic or non-aromatic ring. They are preferably acyclic.

More particularly, the liquid unsaturated fatty alcohols of the invention are chosen from oleyl alcohol, linoleyl alcohol, linolenyl alcohol and undecylenyl alcohol.

Oleyl alcohol is very particularly preferred.

The term "liquid fatty ester" means an ester derived from a fatty acid and/or from a fatty alcohol and that is liquid at ordinary temperature (25° C.) and at atmospheric pressure (760 mmHg; i.e. $1.013 \times 10^5$ Pa).

The esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds which contain several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

Finally, natural or synthetic esters of monoacids, diacids or triacids with glycerol may also be used. Among these, mention may be made of plant oils.

As oils of plant origin or synthetic triglycerides that may be used in the composition of the invention as liquid fatty esters, examples that may be mentioned include:
triglyceride oils of plant or synthetic origin, such as liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

Liquid fatty esters derived from monoalcohols will preferably be used as esters according to the invention.

Isopropyl myristate and isopropyl palmitate are particularly preferred.

The term "liquid silicone" means an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, especially liquid polydimethylsiloxanes (PDMSs) and liquid polyorganosiloxanes comprising at least one aryl group.

These silicones may also be organomodified. The organomodified silicones that can be used in accordance with the invention are liquid silicones as defined above and comprising in their structure one or more organofunctional groups attached via a hydrocarbon-based group.

Organopolysiloxanes are defined in greater detail in Walter Noll's "Chemistry and Technology of Silicones" (1968) Academic Press. They may be volatile or non-volatile.

When they are volatile, the silicones are more particularly chosen from those having a boiling point of between 60° C. and 260° C., and more particularly still from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof.

Mention may also be made of cyclocopolymers of the dimethylsiloxane/methylalkylsiloxane type, such as Silicone Volatile® FZ 3109 sold by the company Union Carbide, of formula:

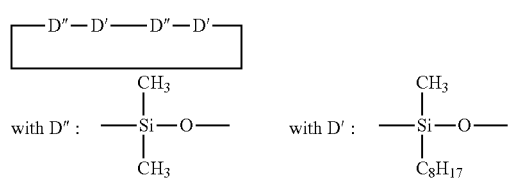

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, Janurary 76, pp. 27-32, Todd & Byers "Volatile Silicone Fluids for Cosmetics". The viscosity of the silicones is measured at 25° C. according to ASTM standard 445 Appendix C.

Non-volatile polydialkylsiloxanes may also be used.

These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from the company Dow Corning, such as DC200 with a viscosity of 60 000 mm2/s;
the Viscasil® oils from General Electric and certain oils of the SF series (SF 96, SF 18) from General Electric.

Mention may also be made of polydimethylsiloxanes containing dimethylsilanol end groups known under the name Dimethiconol (CTFA), such as the oils of the 48 series from the company Rhodia.

Among the silicones containing aryl groups are polydiarylsiloxanes, especially polydiphenylsiloxanes and polyalkylarylsiloxanes. Examples that may be mentioned include the products sold under the following names:
the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722, and L77 from the company Union Carbide.

The liquid fatty acids are preferably unsaturated and/or branched fatty acids. Mention may be made in particular of oleic acid.

The liquid fatty ethers are chosen from liquid dialkyl ethers such as dicaprylyl ether.

The fatty substances may be non-liquid at room temperature and at atmospheric pressure.

The term "non-liquid" preferably means a solid compound or a compound that has a viscosity of greater than 2 Pa·s at a temperature of 25° C. and at a shear rate of 1 $s_{-1}$.

More particularly, the non-liquid fatty substances are chosen from fatty alcohols, esters of fatty acids and/or of fatty alcohols, non-silicone waxes, silicones and fatty ethers, which are non-liquid and preferably solid.

The non-liquid fatty alcohols that are suitable for use in the invention are more particularly chosen from saturated or unsaturated, linear or branched alcohols comprising from 8 to 30 carbon atoms. Mention may be made, for example, of cetyl alcohol, stearyl alcohol and a mixture thereof (cetylstearyl alcohol).

As regards the non-liquid esters of fatty acids and/or of fatty alcohols, mention may be made especially of solid esters derived from $C_9$-$C_{26}$ fatty acids and from $C_9$-$C_{26}$ fatty alcohols.

Among these esters, mention may be made of octyldodecyl behenate; isocetyl behenate; cetyl lactate; stearyl octanoate; octyl octanoate; cetyl octanoate; decyl oleate; myristyl stearate; octyl palmitate; octyl pelargonate; octyl stearate; alkyl myristates such as cetyl, myristyl or stearyl myristate; hexyl stearate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may especially be made of: diethyl sebacate; diisopropyl sebacate; diisopropyl adipate; di-n-propyl adipate; dioctyl adipate; dioctyl maleate.

Among all the additional esters mentioned above, it is preferred to use myristyl, cetyl or stearyl palmitates, alkyl myristates such as cetyl myristate, and stearyl myristyl myristate.

The (non-silicone) wax(es) is (are) selected in particular from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The non-liquid silicones in accordance with the invention may be present in the form of waxes, resins or gums.

Preferably, the non-liquid silicone is chosen from polydialkylsiloxanes, especially polydimethylsiloxanes (PDMSs), and organomodified polysiloxanes comprising at least one functional group chosen from poly(oxyalkylene) groups, amino groups and alkoxy groups.

The silicone gums that can be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:
  mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
  mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
  mixtures of two PDMSs with different viscosities, and more particularly of a PDMS gum and a PDMS oil, such as the product SF 1236 from the company General Electric. The product SF 1236 is a mixture of a gum SE 30 defined above, with a viscosity of 20 m²/s and of an oil SF 96 with a viscosity of $5\times10^{-6}$ m²/s. This product preferably comprises 15% of gum SE 30 and 85% of an oil SF 96.

The organopolysiloxane resins that can be used in accordance with the invention are crosslinked siloxane systems containing the following units:
  $R_2SiO_{2/2}$, $R_3SiO_{1/2}$, $RSiO_{3/2}$ and $SiO_{4/2}$
in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu Among the additional organomodified silicones, mention may be made of polyorganosiloxanes comprising:
  substituted or unsubstituted amine groups, for instance the products sold under the names Q2 8220 and Dow Corning 929 or 939 by the company Dow Corning. The substituted amine groups are, in particular, $C_1$-$C_4$ aminoalkyl groups;
  alkoxylated groups, such as the product sold under the name Abil Wax® 2428, 2434 and 2440 by the company Goldschmidt.

The non-liquid fatty ethers are chosen from dialkyl ethers and especially dicetyl ether and distearyl ether, alone or as a mixture.

Preferably, the compositions of the invention contain one or more fatty substances that are liquid at ordinary temperature (25° C.) and at atmospheric pressure (760 mmHg; i.e. $1.013\times10^5$ Pa), optionally combined with one or more fatty substances that are non-liquid under the same conditions.

Preferably, the fatty substance is chosen from liquid petroleum jelly, polydecenes and liquid esters, or mixtures thereof.

According to one particular embodiment, the emulsions (A) and (B) that are useful in the context of the present invention each comprise an amount of fatty substances free of carboxylic acid groups of greater than 25% by weight relative to the total weight of the emulsion. Preferably, the fatty substance concentration ranges from 25% to 70% and better still from 30% to 55% of the total weight of the emulsion.

The concentration of fatty substances free of carboxylic acid groups is at least equal to 25% by weight, preferably between 25% and 70% by weight and more preferably still between 30% and 60% by weight of the total weight of the composition obtained after mixing the two direct emulsions (A) and (B).

The emulsions (A) and (B) also comprise one or more surfactants.

Preferably, the surfactant(s) is (are) selected from nonionic surfactants and anionic surfactants.

The term "anionic surfactant" means a surfactant comprising, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $HPO_2^-$, $PO_2^-$, $POH$, $PO^-$.

As examples of anionic surfactants that may be used in the composition according to the invention, mention may be made of alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, alpha-olefin sulphonates, paraffin sulphonates, alkyl sulphosuccinates, alkyl ether sulphosuccinates, alkylamide sulphosuccinates, alkyl sulphoacetates, acyl sarcosinates, acyl glutamates, alkyl sulphosuccinamates, acyl isethionates and N-acyl taurates; salts of alkyl monoesters of polyglycoside-polycarboxylic acids, acyl lactylates, salts of D-galactosiduronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulphosuccinates.

When the anionic surfactant(s) is (are) in salt form, it (they) may be chosen from alkali metal salts such as the sodium or potassium salt and preferably the sodium salt, the ammonium salts, the amine salts and in particular amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

The alkali metal or alkaline-earth metal salts and in particular the sodium or magnesium salts are preferably used.

The nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
oxyalkylenated ($C_8$-$C_{24}$)alkylphenols;
saturated or unsaturated, linear or branched, oxyalkylenated $C_8$-$C_{30}$ alcohols;
saturated or unsaturated, linear or branched, oxyalkylenated $C_8$-$C_{30}$ amides;
esters of saturated or unsaturated, linear or branched, $C_8$-$C_{30}$ acids and of polyethylene glycols;
polyoxyethylenated esters of saturated or unsaturated, linear or branched, $C_8$-$C_{30}$ acids and of sorbitol;
saturated or unsaturated, oxyethylenated plant oils;
oxyalkylenated silicones;
condensates of ethylene oxide and/or of propylene oxide, inter alia, alone or as mixtures.

The surfactants contain a number of moles of ethylene oxide and/or of propylene oxide of between 1 and 50, preferably between 2 and 30. Advantageously, the nonionic surfactants do not comprise any oxypropylene units.

In accordance with one preferred embodiment of the invention, the oxyalkylenated nonionic surfactants are chosen from oxyethylenated $C_8$-$C_{30}$ alcohols and oxyethylenated $C_8$-$C_{30}$ amines.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

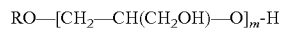

$$RO\text{---}[CH_2\text{---}CH(CH_2OH)\text{---}O]_m\text{-}H$$

in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferably, the surfactant present in each of the emulsions (A) and (B) is a nonionic surfactant.

The surfactant content in each of the emulsions (A) and (B) more particularly represents from 0.1% to 50% by weight, preferably from 0.5% to 30% by weight and better still from 1% to 20% by weight relative to the total weight of said emulsion.

The emulsion (A) comprises one or more oxidizing agents. More particularly, the oxidizing agent(s) is (are) chosen from hydrogen peroxide, urea peroxide, alkali metal bromates or ferricyanides, peroxygenated salts, for instance persulphates, perborates, peracids and precursors thereof and percarbonates of alkali metals or alkaline-earth metals.

This oxidizing agent is advantageously constituted by hydrogen peroxide, especially as an aqueous solution (aqueous hydrogen peroxide solution), the titre of which may range more particularly from 1 to 40 volumes and more preferably still from 5 to 40 volumes.

As a function of the desired degree of lightening, the oxidizing agent may also comprise an oxidizing agent preferably chosen from peroxygenated salts.

In one variant of the invention, the emulsion (A) contains, as oxidizing agent, only hydrogen peroxide.

The emulsion (B) comprises one or more alkaline agents. This or these alkaline agent(s) is (are) generally such that the $pK_b$ at 25° C. is less than 12, preferably less than 10 and more advantageously still less than 6. It should be noted that it is the $pK_b$ corresponding to the function of highest basicity.

The alkaline agent may be chosen from ammonia, inorganic bases, organic amines and organic amine salts, alone or as a mixture.

Examples of organic amines that may be mentioned are organic amines comprising one or two primary, secondary or tertiary amine functions, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable are the organic amines of the following formula:

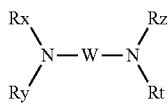

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

According to another variant of the invention, the organic amine is chosen from amino acids.

More particularly, the amino acids that may be used are of natural or synthetic origin, in their L, D or racemic form, and comprise at least one acid function chosen more particularly from carboxylic acid, sulphonic acid, phosphonic acid or phosphoric acid functions. The amino acids may be in neutral or ionic form.

Advantageously, the amino acids are basic amino acids comprising an additional amine function optionally included in a ring or in a ureido function.

Such basic amino acids are preferably chosen from those corresponding to formula (I) below:

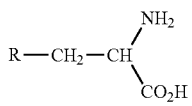

(I)

in which R denotes a group chosen from:

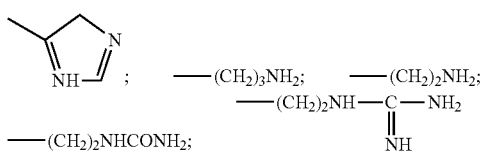
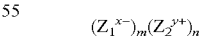

The compounds corresponding to formula (I) are histidine, lysine, arginine, ornithine and citrulline.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

According to one preferred variant of the invention, the organic amine is chosen from basic amino acids. The amino acids that are particularly preferred are arginine, lysine and histidine, or mixtures thereof.

According to another variant of the invention, the organic amine is chosen from organic amines of heterocyclic type. Besides histidine that has already been mentioned in the amino acids, mention may in particular be made of pyridine, piperidine, imidazole, 1,2,4-triazole, tetrazole and benzimidazole.

According to another variant of the invention, the organic amine is chosen from amino acid dipeptides. As amino acid dipeptides that may be used in the present invention, mention may be made especially of carnosine, anserine and baleine.

According to another variant of the invention, the organic amine is chosen from compounds comprising a guanidine function. As amines of this type that may be used in the present invention, besides arginine which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulphonic acid.

Preferably, the organic amine is an alkanolamine. More preferentially, the organic amine is chosen from 2-amino-2-methyl-1-propanol, monoethanolamine, or mixtures thereof. More preferentially still, the organic amine is monoethanolamine.

The alkaline agent may be an organic amine in salt form. For the purposes of the present invention, the term "organic amine salt" means organic or inorganic salts of an organic amine as described above.

Preferably, the organic salts are chosen from organic acid salts such as citrates, lactates, glycolates, gluconates, acetates, propionates, fumarates, oxalates and tartrates.

Preferably, inorganic salts are chosen from hydrohalides (for example hydrochlorides), carbonates, hydrogen carbonates, sulphates, hydrogen phosphates and phosphates.

For the purposes of the present invention, the term "inorganic base" means any compound bearing in its structure one or more elements from columns 1 to 13 of the Periodic Table of the Elements other than hydrogen, not simultaneously comprising carbon and hydrogen atoms.

According to one particular embodiment of the invention, the inorganic base contains one or more elements from columns 1 and 2 of the Periodic Table of the Elements other than hydrogen.

In one preferred variant, the inorganic base has the following structure:

$$(Z_1^{x-})_m(Z_2^{y+})_n$$

in which:

$Z_2$ denotes a metal from columns 1 to 13 and preferably from column 1 or 2 of the Periodic Table of the Elements, for instance sodium or potassium;

$Z_1^{x-}$ denotes an anion chosen from the ions $CO_3^{2-}$, $OH^-$, $HCO_3^{2-}$, $SiO_3^{2-}$, $HPO_4^{2-}$, $PO_4^{3-}$ and $B_4O_7^{2-}$, and preferably from the ions $CO_3^{2-}$, $OH^-$ and $SiO_3^{2-}$;

x denotes 1, 2 or 3;

y denotes 1, 2, 3 or 4;

m and n denote, independently of each other, 1, 2, 3 or 4; with $n \cdot y = m \cdot x$.

Preferably, the inorganic base corresponds to the following formula:

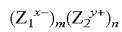

in which $Z_2$ denotes a metal from columns 1 and 2 of the Periodic Table of the Elements; $Z_1^{x-}$ denotes an anion chosen from the ions $CO_3^{2-}$, $OH^-$ and $SiO_3^{2-}$, x is 1, y denotes 1 or 2, and m and n denote, independently of each other, 1 or 2 with n·y=m·x.

As inorganic bases that may be used according to the invention, mention may be made of sodium bicarbonate, potassium carbonate, sodium hydroxide, potassium hydroxide, sodium metasilicate and potassium metasilicate.

Ammonium salts may also be used as alkaline agent. The ammonium salts are preferably chosen from the following acid salts: carbonate, bicarbonate.

According to one particular embodiment, the emulsion (B) contains, as alkaline agents, at least one organic amine, preferably at least one alkanolamine.

When the composition contains several alkaline agents, including an alkanolamine and aqueous ammonia or a salt thereof, the organic amine(s) is (are) preferably in weight majority relative to the amount of ammonia.

Generally, the emulsion (B) has an alkaline agent content ranging from 0.1% to 40% by weight, preferably from 0.5% to 20% by weight and better still from 1% to 10% by weight relative to the total weight of said emulsion.

The emulsions (A) and (B) may also contain various adjuvants conventionally used in hair lightening and/or dyeing compositions, such as anionic, cationic, nonionic, amphoteric or zwitterionic polymers or mixtures thereof; inorganic thickeners, and in particular fillers such as clays and talc; organic thickeners with, in particular, anionic, cationic, nonionic and amphoteric polymeric associative thickeners; antioxidants; penetrants; sequestrants; fragrances; dispersants; film-forming agents; preserving agents; opacifiers.

They may optionally comprise an organic solvent. Examples of organic solvents that may be mentioned include linear or branched $C_2$-$C_4$ alkanols, such as ethanol and isopropanol; polyols and polyol ethers, for instance 2-butoxyethanol, glycerol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The emulsions (A) and (B) may also comprise one or more acidifying agents.

Among the acidifying agents, examples that may be mentioned include inorganic or organic acids, for instance hydrochloric acid, orthophosphoric acid, sulphuric acid, carboxylic acids, for instance acetic acid, tartaric acid, citric acid or lactic acid, and sulphonic acids.

Usually, the pH of the aqueous phase of emulsion (A) is less than 7. The pH of the aqueous phase of emulsion (B) is preferably such that the pH of the composition obtained after mixing with emulsion (A) is between 7 and 12, preferably between 8 and 11. The pH of emulsion (B) is preferably between 7 and 12.

According to one particular embodiment, the emulsions (A) and (B) may be prepared via conventional processes for preparing direct emulsions, but also via a PIT process. In one variant of the invention, the emulsions (A) and (B) are prepared via a PIT process.

According to this particular embodiment, the principle of emulsification by means of the phase inversion temperature (or PIT) is, in its principle, well known to those skilled in the art; it was described in 1968 by K. Shinoda (J. Chem. Soc. Jpn., 1968, 89, 435). It has been shown that this emulsification technique allows stable, fine emulsions to be obtained (K. Shinoda and H. Saito, J. Colloid Interface Sci., 1969, 30, 258). This technology was applied in cosmetics as early as 1972 by Mitsui et al. ("Application of the phase-inversion-temperature method to the emulsification of cosmetics"; T. Mitsui, Y. Machida and F. Harusawa, American Cosmet. Jpn., 1972, 87, 33).

The principle of this technique is as follows: a mixture of an aqueous phase and an oily phase is prepared and is brought to a temperature above the PIT temperature, the phase inversion temperature of the system, which is the temperature at which the equilibrium between the hydrophilic and lipophilic properties of the emulsifier(s) used is reached; at elevated temperature, i.e. above the phase inversion temperature (>PIT), the emulsion is of water-in-oil type, and, during its cooling, this emulsion inverts at the phase inversion temperature, to become an emulsion of oil-in-water type, doing so by passing previously through a state of microemulsion. This process makes it readily possible to obtain emulsions with a diameter of less than 4 μm, preferably of less than 1 μm.

In greater detail, it is possible to operate as follows in order to obtain a PIT emulsion:

1) Weigh out in a container all the constituents of the direct emulsion (A) or of the direct emulsion (B).

2) Homogenize the mixture, using for example a 350 rpm Rayneri blender, and heat by gradually increasing the temperature using a water bath, up to a temperature greater than the phase inversion temperature T1, in other words until a transparent or translucent phase is obtained (microemulsion zone or lamellar phase) and then until a more viscous phase is obtained, which indicates that the inverse emulsion (W/O) has been obtained.

3) Stop the heating but continue stirring until the emulsion has cooled to room temperature, passing through the phase inversion temperature T1, in other words the temperature at which a fine 0/W emulsion is formed.

4) When the temperature has fallen below the phase inversion temperature (T1) zone again, add any additives and the heat-sensitive starting materials.

A stable final composition is obtained in which the lipophilic-phase droplets are fine, with sizes of 10 to 200 nm.

In the zone where a microemulsion (translucent mixture) is formed, the hydrophilic and hydrophobic interactions are balanced, since the surfactant has a tendency to form both direct micelles and inverse micelles. By heating beyond this zone, a W/O emulsion is formed, because the surfactant promotes the formation of a water-in-oil emulsion. Subsequently, on cooling below the phase inversion zone, the emulsion becomes a direct (O/W) emulsion.

Emulsification by phase inversion is explained in detail in the publication by T. Förster, W. von Rybinski and A. Wadle: Influence of microemulsion phases on the preparation of fine disperse emulsions, Advances in Colloid and Interface Sciences, 58, 119-149, 1995, which is cited herein for reference.

Emulsion (B) may comprise one or more dyes. This or these dye(s) may be direct dyes or oxidation dyes.

The oxidation dyes are generally chosen from oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-paraphenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and their addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-βhydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bisphenylalkylenediamines that may be mentioned, for example, are N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chloro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2801308. Examples that may be mentioned include pyrazolo[1,5-a]pyrid-3-ylamine, 2-acetylaminopyrazolo[1,5-a]pyrid-3-ylamine,2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]-pyrid-7-yl)methanol, 2-(3-aminopyrazolo[1,5-a]pyrid-5-yl)ethanol, 2-(3-aminopyrazolo-[1,5-a]pyrid-7-yl)ethanol, 2-(3-aminopyrazolo[1,5-a]pyrid-2-yl)methanol, 3,6-diamino-pyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methyl-pyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts. 4,5-Diamino-1-(β-methoxyethyl)pyrazole may also be used.

A heterocyclic base that may also be mentioned is 2,3-diamino-6,7-dihydro-1H,5H-pyrazolo[1,2-a]pyrazol-1-one or a salt thereof.

The direct emulsion (B) that is useful in the context of the invention may optionally comprise one or more couplers advantageously chosen from those conventionally used for the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylamino-benzene, sesamol, 1-β-hydroxyethylamino-3,4-methylenedioxybenzene, α-naphthol, 2-methyl-1- naphthol, 6-hydroxyindole, 4-hydroxyindole, 4-hydroxy-N-methyindole, 2-amino-3-hydroxypyridine, 6-hydroxybenzomorpholine, 3,5-diamino-2,6-dimethoxy-pyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methyl-pyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulphates, citrates, succinates, tartrates, lactates, tosylates, benzenesulphonates, phosphates and acetates.

The oxidation base(s), if they are present, each advantageously represent from 0.0001% to 10% by weight and preferably from 0.005% to 5% by weight relative to the total weight of the emulsion (B).

The coupler(s), if they are present, each advantageously represent from 0.0001% to 10% by weight and preferably from 0.005% to 5% by weight relative to the total weight of the emulsion (B).

As regards the direct dyes, these dyes are more particularly chosen from ionic and nonionic species, preferably cationic or nonionic species.

Examples of suitable direct dyes that may be mentioned include the following direct dyes: azo dyes; methine dyes; carbonyl dyes; azine dyes; nitro (hetero)aryl dyes; tri(hetero)arylmethane dyes; porphyrin dyes; phthalocyanine dyes, and natural direct dyes, alone or as mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence selected from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro (hetero)aromatic dyes are more particularly nitrobenzene or nitropyridine direct dyes.

As regards the dyes of porphyrin or phthalocyanine type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures.

These dyes may be monochromophoric dyes (i.e. comprising only one dye) or polychromophoric, preferably dichromophoric or trichromophoric, dyes; the chromophores may be identical or different, and from the same chemical family or otherwise. It should be noted that a polychromophoric dye comprises several radicals each derived from a molecule that absorbs in the visible region between 400 and 800 nm. Furthermore, this absorbance of the dye does not require any prior oxidation thereof, or combination with any other chemical species.

In the case of polychromophoric dyes, the chromophores are connected together by means of at least one linker, which may be cationic or non-cationic.

Among the benzene direct dyes that may be used according to the invention, mention may be made in a non-limiting manner of the following compounds:

1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene; and
1-hydroxy-4-β-hydroxyethylamino-3-nitrobenzene.

Among the azo, azomethine, methine and tetraazapentamethine direct dyes that may be used according to the invention, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Among these, mention may also be made of the following compounds:

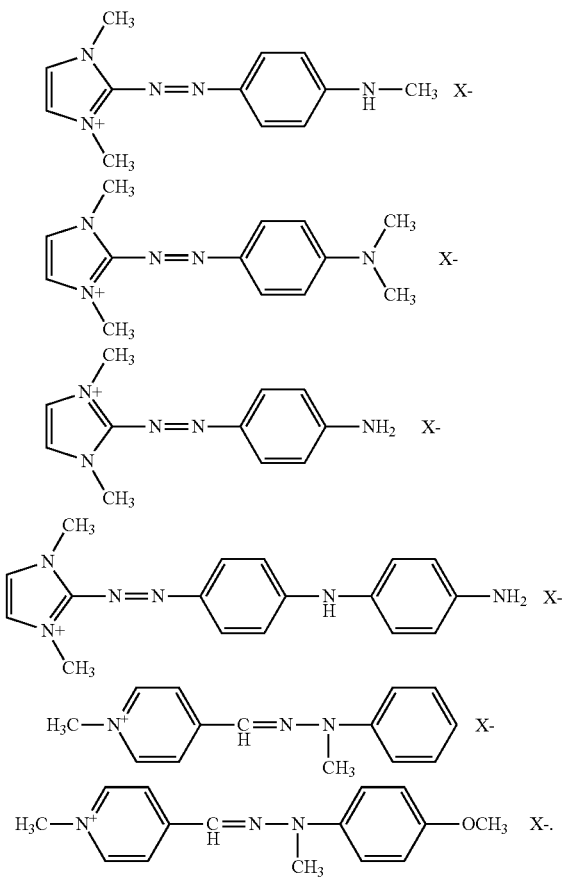

Among the azo direct dyes that may also be mentioned are the following dyes, described in the Colour Index International, 3rd edition:
Disperse Red 17
Basic Red 22
Basic Red 76
Basic Yellow 57
Basic Brown 16
Basic Brown 17
Disperse Black 9.

Mention may also be made of 1-(4'-aminodiphenylazo)-2-methyl-4-bis(β-hydroxyethyl)aminobenzene.

Among the quinone direct dyes that may be mentioned are the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and also the following compounds:
   1-N-methylmorpholiniumpropylamino-4-hydroxyanthraquinone;
   1-aminopropylamino-4-methylaminoanthraquinone;
   1-aminopropylaminoanthraquinone;
   5-6-hydroxyethyl-1,4-diaminoanthraquinone;
   2-aminoethylaminoanthraquinone; and
   1,4-bis(β,γ-dihydroxypropylamino)anthraquinone.

Among the azine dyes that may be mentioned are the following compounds:
Basic Blue 17
Basic Red 2.

Among the triarylmethane dyes that may be used according to the invention, mention may be made of the following compounds:
Basic Green 1
Basic Violet 3
Basic Violet 14
Basic Blue 7
Basic Blue 26

Among the indoamine dyes that can be used according to the invention, mention may be made of the following compounds:
   2-β-hydroxyethylamino-5-[bis(β-4'-hydroxyethyl)amino]anilino-1,4-benzoquinone;
   2-β-hydroxyethylamino-5-(2'-methoxy-4'-amino)anilino-1,4-benzoquinone;
   3-N-(2'-chloro-4'-hydroxy)phenylacetylamino-6-methoxy-1,4-benzoquinone imine;
   3-N-(3'-chloro-4'-methylamino)phenylureido-6-methyl-1,4-benzoquinone imine; and
   3-[4'-N-(ethyl,carbamylmethyl)amino]phenylureido-6-methyl-1,4-benzoquinone imine.

Among the dyes of tetraazapentamethine type that may be used according to the invention, mention may be made of the following compounds given in the table below, An being defined as previously:

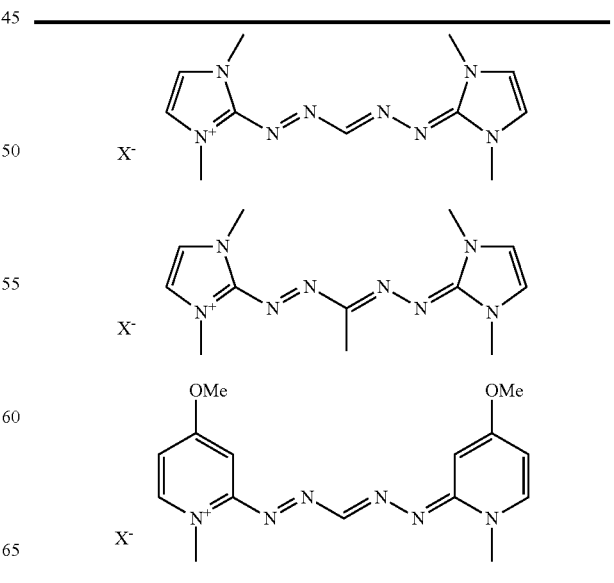

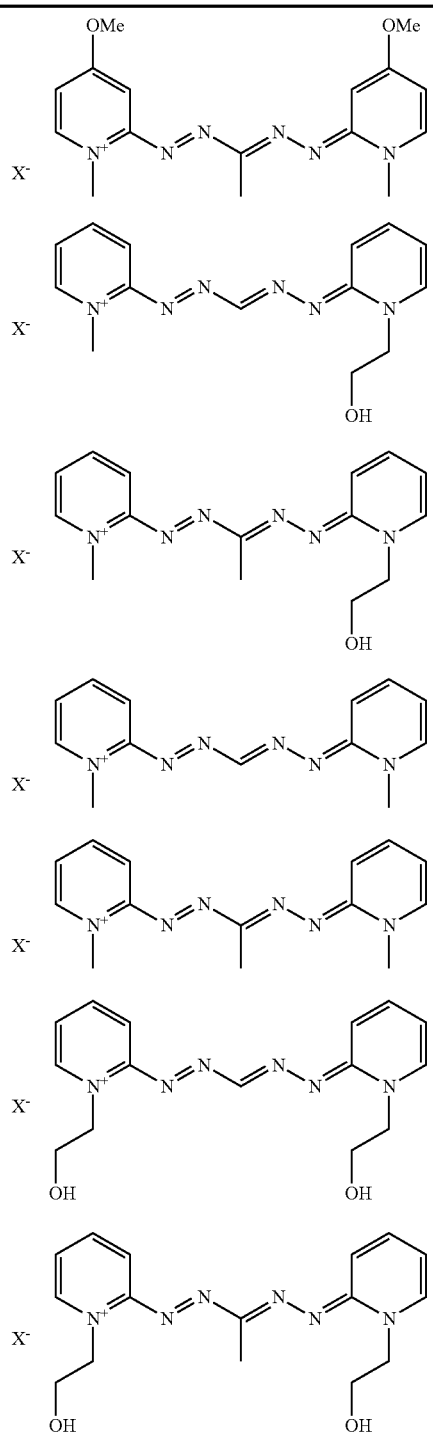

X⁻ represents an anion preferably chosen from chloride, iodide, methyl sulphate, ethyl sulphate, acetate and perchlorate.

Among the polychromophoric dyes, reference may be made more particularly to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is also possible to use the cationic direct dyes mentioned in patent applications: EP 1 006 153, which describes dyes comprising two chromophores of anthraquinone type connected via a cationic linker; EP 1 433 472, EP 1 433 474, EP 1 433 471 and EP 1 433 473, which describe identical or different dichromophoric dyes, connected via a cationic or non-cationic linker, and also EP 6 291 333, which especially describes dyes comprising three chromophores, one of them being an anthraquinone chromophore, to which are attached two chromophores of azo or diazacarbocyanin type or an isomer thereof.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin, orceins, haematin, haematoxylin, brasilein and brasilin. Extracts or decoctions containing these natural dyes and in particular henna-based poultices or extracts, may also be used.

When they are present, the direct dye(s) more particularly represent(s) from 0.0001% to 10% by weight and preferably from 0.005% to 5% by weight of the total weight of the composition.

The emulsion (B) may comprise peroxygenated compounds such as urea peroxide, peroxygenated salts, for instance persulphates, perborates, peracids and precursors thereof and percarbonates of alkali metals or alkaline-earth metals. In this case, it may be used especially in processes for lightening keratin fibres.

According to one variant of the invention, the emulsion (B) does not contain peroxygenated compounds.

According to one variant, the emulsions (A) and/or (B) comprise one or more thickeners. Thickeners that may be mentioned include carbomers, carboxyvinyl polymers containing hydrophobic groups, thickeners containing sugar units, statistical amphiphilic AMPS polymers modified by reaction with a $C_6$-$C_{22}$ n-monoalkylamine or di-n-alkylamine, and such as those described in patent application WO 00/31154. These polymers may also contain other ethylenically unsaturated hydrophilic monomers chosen, for example, from (meth)acrylic acids, β-substituted alkyl derivatives thereof or esters thereof obtained with monoalcohols or monoalkylene or polyalkylene glycols, (meth)acrylamides, vinylpyrrolidone, maleic anhydride, itaconic acid or maleic acid, or mixtures of these compounds.

The process of the invention may be performed by applying to the keratin materials the emulsion (A) and the emulsion (B), in any order, successively and without intermediate rinsing.

According to one embodiment of the process of the invention, a composition obtained by extemporaneous mixing, at the time of use, of emulsion (A) and of emulsion (B) is applied to the wet or dry keratin materials. According to this embodiment, the weight ratio of the amounts of (A)/(B) ranges from 0.1 to 10, preferably from 0.2 to 3 and better still from 0.3 to 2.

In addition, independently of the variant used, the mixture present on the keratin materials (resulting either from the extemporaneous mixing of (A) and (B) or from the partial or total successive application thereof) is left in place for a time generally from about 1 minute to 1 hour and preferably from 5 minutes to 30 minutes.

The temperature during the process is conventionally between room temperature (between 15 and 25° C.) and 80° C. and preferably between room temperature and 60° C.

After the treatment, the keratin materials are optionally rinsed with water, optionally subjected to washing followed by rinsing with water, and are then dried or left to dry.

Finally, the invention relates to a multi-compartment device comprising, in a first compartment, an emulsion (A), and, in a second, an emulsion (B), these emulsions having been described previously.

Preferably, the keratin materials are human hair.

EXAMPLES

The concentrations are indicated in grams of product in the given form per 100 grams of composition.

1) Lightening Process

| Alkaline composition B (invention) | | |
|---|---|---|
| Phase | Name | B (g %) |
| 1 | Oxyethylenated behenyl alcohol (10 EO) | 6 |
| | Sorbitol | 5 |
| | Liquid petroleum jelly | 44 |
| | Distearyl ether | 5 |
| | Water | 10 |
| 2 | Monoethanolamine | 5.55 |
| | Sodium metabisulphite | 0.7 |
| | L-Ascorbic acid | 0.25 |
| | Diethylenetriaminepentaacetic acid, pentasodium salt as a 40% aqueous solution | 1 |
| | Water | 22.5 |

| Oxidizing compositions A (invention) and C (outside the invention) | | | |
|---|---|---|---|
| Phase | Name | A (g %) | C (g %) |
| 1 | Oxyethylenated behenyl alcohol (10 EO) | 6 | 6 |
| | Sorbitol | 5 | 5 |
| | Liquid petroleum jelly | 44 | — |
| | Distearyl ether | 5 | — |
| | Water | 10 | 59 |
| | Sodium salicylate | 0.035 | 0.035 |
| 2 | Tetrasodium pyrophosphate, 10 $H_2O$ | 0.04 | 0.04 |
| | Etidronic acid, tetrasodium salt as a 30% aqueous solution | 0.2 | 0.2 |
| | Phosphoric acid | 0.1 | 0.1 |
| | Hydrogen peroxide as a 50% aqueous solution (200 vol. aqueous hydrogen peroxide solution) | 24 | 24 |
| | Water | 5.625 | 5.625 |

Procedure:

All the compositions are prepared in the following manner:

Phase 1 is heated on a water bath to 80° C., while using a Rayneri homogenizer (400 rpm). In the case of compositions A to C, the PIT temperature is 68° C.

After returning to room temperature, the ingredients of phase 2 are introduced.

Application to Lock of Hair

At the time of use, 10 g of composition B are mixed with 20 g of composition A or C.

The mixture (pH≈9.3±0.1) is then applied to a lock of natural chestnut hair (tone depth=4). The bath ratio is 10 g of mixture per 1 g of hair. The leave-on time is 35 minutes at 27° C. After this time, the locks are rinsed and then washed with Elsève multivitamin shampoo.

The dyeing result is evaluated using a MINOLTA CM2600D spectrocolorimeter.

As shown in the table below, the lock treated with the mixture B+A (49% of fatty substance in the mixture) is lightened better than the lock lightened with the mixture B+C (16.33% of fatty substance in the mixture).

| | L* (D65) | a* (D65) | b* (D65) | ΔE*ab |
|---|---|---|---|---|
| Untreated hair | 20.61 | 3.98 | 5.17 | — |
| Hair treated with the mixture of the invention B + A | 30.48 | 9.28 | 15.79 | 15.43 |
| Hair treated with the mixture of the prior art B + C | 27.15 | 8.52 | 12.08 | 10.54 |

2) Dyeing Process

| Dyeing composition E | | |
|---|---|---|
| Phase | Name | E (g %) |
| 1 | Oxyethylenated behenyl alcohol (10 EO) | 6 |
| | Sorbitol | 5 |
| | Liquid petroleum jelly | 44 |
| | Distearyl ether | 5 |
| | Water | 10 |
| 2 | Monoethanolamine | 5.55 |
| | Sodium metabisulphite | 0.7 |
| | L-Ascorbic acid | 0.25 |
| | Diethylenetriaminepentaacetic acid, pentasodium salt as a 40% aqueous solution | 1 |
| | 1,4-diaminobenzene | 0.31 |
| | 1,3-dihydroxybenzene (resorcinol) | 0.29 |
| | 1-hydroxy-3-aminobenzene | 0.04 |
| | 1-β-hydroxyethyloxy-2,4-diaminobenzene dihydrochloride | 0.012 |
| | 1,3-Bis[(4-aminophenyl)(2-hydroxyethyl)amino]-2-propanol tetrahydrochloride | 0.055 |
| | N,N-Bis(2-hydroxyethyl)-p-phenylenediamine sulphate, 1 $H_2O$ | 0.045 |
| | Water | 21.748 |

Procedure:

Composition E is prepared in the following manner:

Phase 1 is heated on a water bath to 80° C., while using a Rayneri homogenizer (400 rpm). The PIT temperature is 68° C.

It is cooled. When the temperature reaches 45° C., the ingredients of phase 2 are introduced.

| Oxidizing compositions D (invention) and F (outside the invention) | | | |
|---|---|---|---|
| Phase | Name | D (g %) | F (g %) |
| 1 | Oxyethylenated behenyl alcohol (10 EO) | 6 | 6 |
| | Sorbitol | 5 | 5 |
| | Liquid petroleum jelly | 44 | — |
| | Distearyl ether | 5 | — |
| | Water | 10 | 59 |
| 2 | Sodium salicylate | 0.035 | 0.035 |
| | Tetrasodium pyrophosphate, 10 $H_2O$ | 0.04 | 0.04 |
| | Etidronic acid, tetrasodium salt as a 30% aqueous solution | 0.2 | 0.2 |
| | Phosphoric acid | 0.1 | 0.1 |
| | Hydrogen peroxide as a 50% solution (200 vol. aqueous hydrogen peroxide solution) | 12 | 12 |
| | Water | 17.625 | 17.625 |

Procedure:

All the compositions are prepared in the following manner:

Phase 1 is heated on a water bath to 80° C., while using a Rayneri homogenizer (400 rpm). In the case of compositions D and F, the PIT temperature is 68° C.

After returning to room temperature, the ingredients of phase 2 are introduced.

Application to Lock of Hair

At the time of use, 12 g of composition E are mixed with 18 g of composition D or F.

The mixture (pH≈9.8±0.1) is then applied to a lock of natural hair containing 90% grey hair (NG). The bath ratio is 10 g of mixture per 1 g of hair. The leave-on time is 30 minutes at 27° C. After this time, the locks are rinsed and then washed with Elsève multivitamin shampoo.

The dyeing result is evaluated using a MINOLTA CM2600D spectrocolorimeter.

As shown in the table below, the uptake into the locks treated with the mixture E+D (49% of fatty substance in the mixture) is more powerful than that into locks treated with the mixture E+F (19.6% of fatty substance in the mixture).

|  | L* (D65) | a* (D65) | b* (D65) | ΔE*ab |
|---|---|---|---|---|
| Untreated NG | 57.26 | 1.23 | 12.4 | — |
| NG treated with the mixture E + D (invention) | 28.26 | 4.41 | 5.36 | 30.02 |
| NG treated with the mixture E + F | 31.21 | 3.62 | 7.14 | 26.68 |

The invention claimed is:

1. A method for the lightening and/or lightening dyeing of keratin materials, comprising treating said keratin fibers with:
   a) at least one direct emulsion (A) comprising at least one fatty substance free of carboxylic acid groups, at least one surfactant, water in an amount greater than about 5% by weight of the total weight of the emulsion, and at least one oxidizing agent; and
   b) at least one direct emulsion (B) comprising at least one fatty substance free of carboxylic acid groups, at least one surfactant, water in an amount greater than about 5% by weight of the total weight of the emulsion, and at least one alkaline agent;
   wherein the concentration of the fatty substances free of carboxylic acid groups is equal to about 25% by weight or more of the total weight of the composition obtained after mixing direct emulsions (A) and (B).

2. The method according to claim 1, wherein the at least one fatty substance is chosen from hydrocarbons, fatty alcohols, fatty esters, silicones, and fatty ethers, and mixtures thereof.

3. The method according to claim 1, wherein the at least one fatty substance is chosen from fatty substances which are liquid or non-liquid at room temperature and at atmospheric pressure.

4. The method according to claim 1, wherein the at least one fatty substance is chosen from liquid petroleum jelly, polydecenes, liquid esters, or mixtures thereof.

5. The method according to claim 1, wherein the emulsions (A) and (B) each comprise at least one fatty substance free of carboxylic acid groups in an amount greater than about 25% by weight relative to the total weight of the emulsion.

6. The method according to claim 1, wherein the at least one surfactant is chosen from nonionic surfactants and anionic surfactants.

7. The method according to claim 6, wherein the anionic surfactants are chosen from alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, alpha-olefin sulphonates, paraffin sulphonates, alkyl sulphosuccinates, alkyl ether sulphosuccinates, alkylamide sulphosuccinates, alkyl sulphoacetates, acyl sarcosinates, acyl glutamates, alkyl sulphosuccinamates, acyl isethionates and N-acyl taurates, salts of alkyl monoesters of polyglycoside-polycarboxylic acids, acyl lactylates, salts of D-galactosiduronic acids, salts of alkyl ether carboxylic acids, salts of alkylaryl ether carboxylic acids, salts of alkylamido ether carboxylic acids, corresponding non-salified forms thereof, alkyl and acyl groups thereof comprising from 6 to 24 carbon atoms, and aryl group denoting a phenyl group, and mixtures thereof.

8. The method according to claim 6, wherein the nonionic surfactants is chosen from monooxyalkylenated or polyoxyalkylenated nonionic surfactants, and monoglycerolated or polyglycerolated nonionic surfactants.

9. The method according to claim 1, wherein the at least one oxidizing agent is chosen from hydrogen peroxide, urea peroxide, alkali metal bromates or ferricyanides, peroxygenated salts, peracids and precursors thereof, and percarbonates of alkali metals or alkaline-earth metals.

10. The method according to claim 1, wherein the at least one alkaline agent is chosen from ammonia, organic amines, inorganic bases, organic amine salts, and ammonium salts.

11. The method according to claim 10, wherein the alkaline agent is chosen from at least one organic amine.

12. The method according to claim 11, wherein the alkaline agent is chosen from an alkanolamine.

13. The method according to claim 1, wherein the at least one direct emulsion (B) comprises one or more oxidation dyes and/or one or more direct dyes.

14. The method according to claim 1, further comprising a step of applying a composition obtained by extemporaneous mixing, at the time of use, the at least one direct emulsion (A) and at least one direct emulsion (B) to said keratin materials.

15. The method according to claim 1, wherein the at least one direct emulsion (A) and at least one direct emulsion (B), are applied to said keratin materials in any order, successively and without intermediate rinsing.

16. A multi-compartment device comprising,
   in a first compartment:
   a) at least one direct emulsion (A) comprising at least one fatty substance free of carboxylic acid groups, at least one surfactant, water in an amount greater than about 5% by weight of the total weight of the emulsion, and at least one oxidizing agent;
   and in a second compartment:
   b) at least one direct emulsion (B) comprising at least one fatty substance free of carboxylic acid groups, at least one surfactant, water in an amount greater than about 5% by weight of the total weight of the emulsion, and at least one alkaline agent;
   wherein the amount of the fatty substances free of carboxylic acid groups in each of the at least one direct emulsion (A) and (B) is such that it would be equal to about 25% by weight or more of the total weight of the composition obtained after mixing direct emulsions (A) and (B).

* * * * *